US00PP19922P2

(12) United States Plant Patent
Glenn

(10) Patent No.: US PP19,922 P2
(45) Date of Patent: Apr. 14, 2009

(54) WILLOW OAK TREE NAMED 'QPSTJ'

(50) Latin Name: *Quercus phellos*
Varietal Denomination: QPSTJ

(75) Inventor: Michael M. Glenn, Bogart, GA (US)

(73) Assignee: Tree Introductions, Inc., Bishop, GA (US)

( * ) Notice: Subject to any disclaimer, the term of this patent is extended or adjusted under 35 U.S.C. 154(b) by 0 days.

(21) Appl. No.: 11/638,970

(22) Filed: Dec. 13, 2006

(51) Int. Cl.
*A01H 5/00* (2006.01)

(52) U.S. Cl. ..... Plt./225
(58) Field of Classification Search ..... Plt./225
See application file for complete search history.

(56) References Cited

U.S. PATENT DOCUMENTS

PP13,677 P3 3/2003 Glenn
PP18,321 P2 12/2007 Glenn

*Primary Examiner*—Annette H Para
(74) *Attorney, Agent, or Firm*—Klarquist Sparkman, LLP

(57) ABSTRACT

A Willow Oak tree named 'QPSTJ' having an upswept branching habit, dense canopy, dominant central leader, unique red fall color, and relatively fast growth rate, and also capable of being reproduced reliably using softwood cutting methods.

6 Drawing Sheets

Latin name of genus and species: *Quercus phellos.*
Variety denomination: 'QPSTJ'.

BACKGROUND OF THE INVENTION

The present invention relates to a new and distinct variety of *Quercus phellos,* Willow Oak, which has been given the varietal name 'QPSTJ.'

The original tree of this new Willow Oak variety was discovered in 2001 as a chance seedling growing in a cultivated area of a nursery in Oconee County, Ga. It had been purchased as a 12 to 18 inch liner in spring 1997 and at that time planted in a cultivated nursery field. This tree was transplanted to another cultivated field in spring 1999. In winter 2003 it was transplanted to an observation area where it has remained since that time. It is now 9 years old from a seed. The description of this new Willow Oak variety is based on observations of this original tree and of asexually propagated progeny, asexually propagated in Oconee County, Ga., from softwood cuttings. These asexually propagated progeny are being grown at a nursery in Oconee County, Ga.

Common Willow Oak is typically a large deciduous tree with a dense, oblong-oval to rounded crown at maturity. On average it will reach 40' to 60' high and 30' to 40' wide. The largest trees will reach 100' in height with an equal spread. It is native to bottomlands, floodplains and adjacent slopes, and rich uplands from New York to Florida, west to Missouri, Okla. and Texas. It prefers moist, well-drained soil but adapts well to harsh conditions. It is one of the best oaks for the heat, drought, and humidity of the Southeast, but also does well in the more arid Midwest. Willow Oak is hardy in USDA Zones 5–9, but performs best in Zones 6–8. It has survived temperatures as low as −25 degrees F. in Cincinnati, Ohio.

This new Willow Oak variety is distinguished from other Willow Oaks known to the inventor by the following unique combination of characteristics: upswept branching habit, dense canopy, dominant central leader, yellow fall color, and relatively fast growth rate. When discovered in 2001, the original tree of this new variety was in the top twenty-five percent in growth rate of the group of Willow Oak trees planted at the same time at the same size in the same group of seedlings.

BRIEF SUMMARY OF THE INVENTION

In 2001, the original tree of this new Willow Oak variety was successfully propagated by softwood cuttings at my direction. This asexual reproduction was accomplished in Oconee County, Ga. The progeny have demonstrated that the novel characteristics of this new variety are fixed, stable, and reproduce true to type through asexual propagation. These observations confirm that 'QPSTJ' represents a new, distinct, and improved variety of Willow Oak as particularly evidenced by the combination of characteristics described above (upswept branching habit, dense canopy, dominant central leader, yellow fall color, and relatively fast growth rate), and which can be asexually propagated reliably using vegetative propagation techniques.

This new variety of Willow Oak is particularly suited for use as a street tree and for filling large areas such as golf courses, commercial sites, and parks. This new Willow Oak variety will provide a uniform, structurally sound tree, and its rapid growth rate will benefit growers who will profit from a relatively fast growing variety of Willow Oak.

My new variety differs from another variety of Willow Oak, 'QPSTB' (patent pending), in that the branching habit of my new variety is upswept.

BRIEF DESCRIPTION OF THE DRAWINGS

The accompanying photographs illustrate this new Willow Oak variety with color as true as reasonable possible in this type of color photograph.

DETAILED BOTANICAL DESCRIPTION

This invention has not been observed under all possible environmental conditions. The phenotype may vary with variations in growing environment such as temperature, light intensity, day length, rainfall, or nutrient availability, without, however, any variation in genotype. 'QPSTJ' Willow Oak is currently growing at a nursery in Oconee County, Ga. This particular area of Oconee County has a clay loam soil type, is in USDA Hardiness Zone 7(a), and receives average yearly rainfall of 50 inches, although actual rainfall in any given year can range between 30 and 60 inches.

The following is a detailed description of my new variety of Willow Oak with color terminology in accordance with The Royal Horticultural Society (R.H.S.) Colour Chart published by The Royal Horticultural Society in London, England. This description is based on observations of the original tree, at about ten years of age, growing at a nursery site in Oconee County, Ga.

Parentage: Discovered as a chance seedling of unknown origin growing in a cultivated area of a nursery in Oconee County, Ga.

Figure 1:
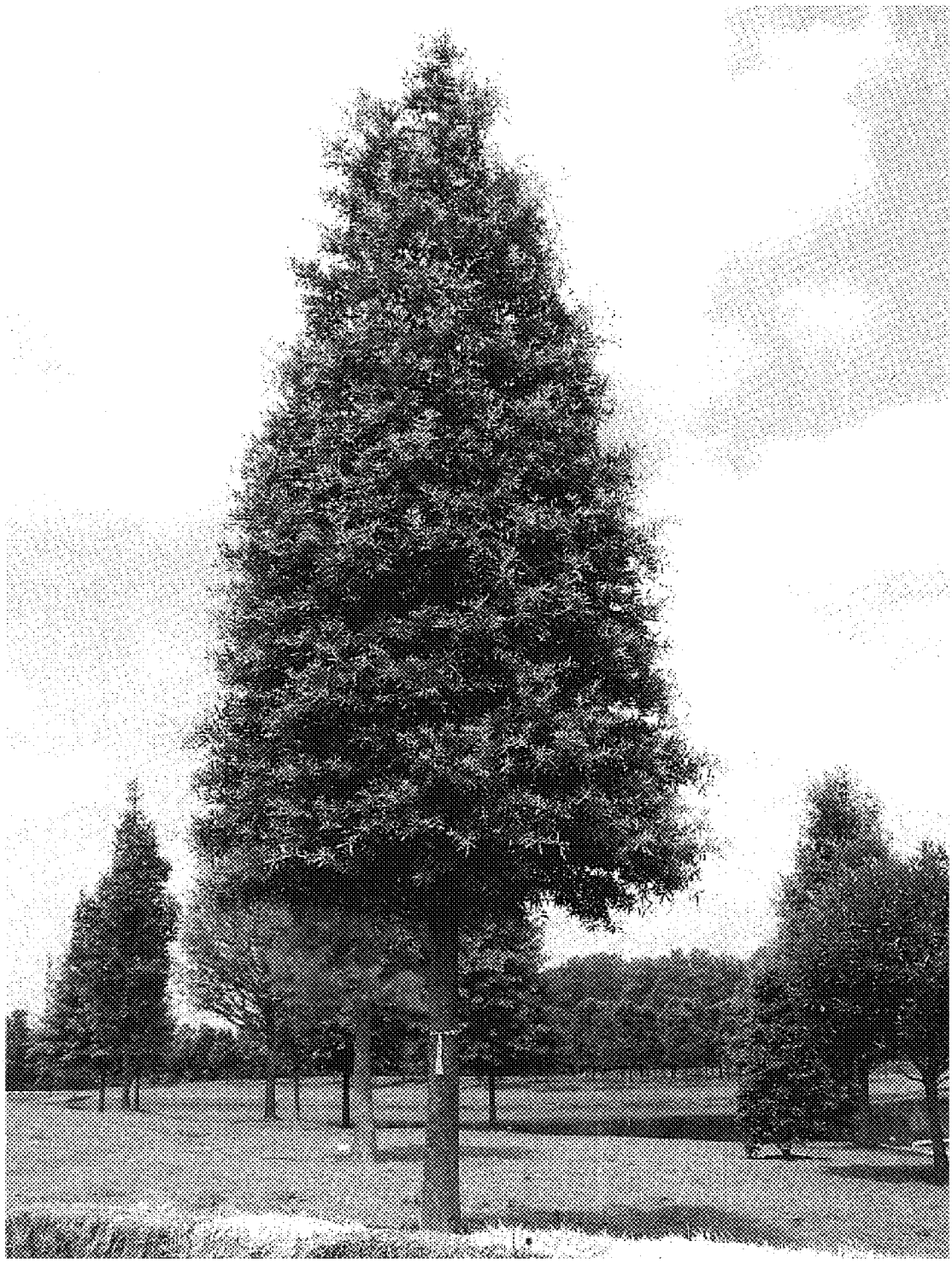
FIG. 1 is a photograph of the original tree of the new variety in summer leaf.
Figure 2:
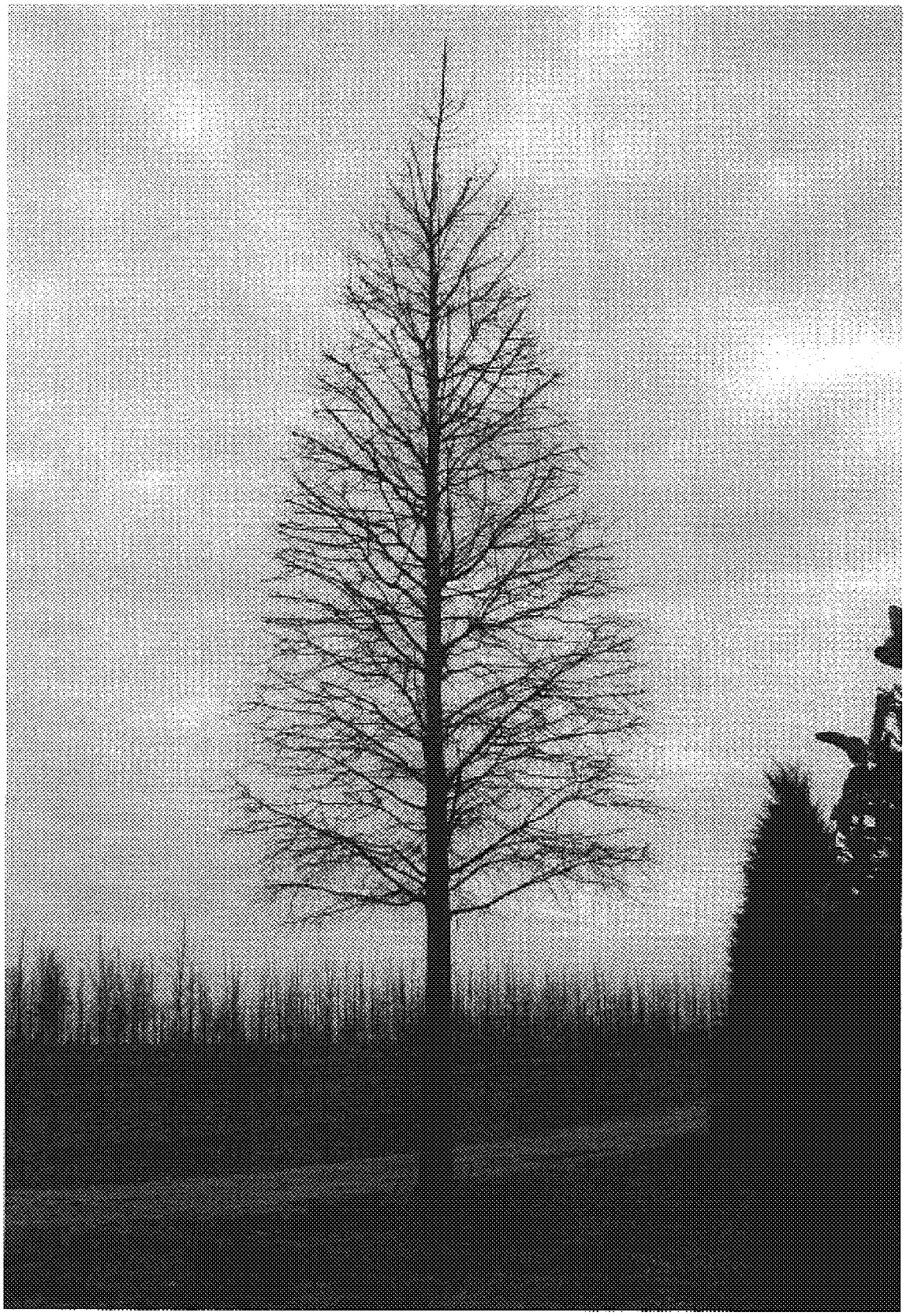
FIG. 2 is a photograph of the original tree of the new variety during winter season.

Tree shape: Dense canopy and a dominant central leader. (See FIGS. 1 and 2)

Size and growth rate: The original tree is currently 9 inches in caliper at 12 inches above the ground, about 28 feet high, and about 12 feet wide, thus providing an overall height to width ration of about 2.33. Prior to transplanting to the observation site, the original tree had an average growth in caliper of about 1.2 inches per year. Root development from time of sticking of a vegetative cutting is approximately six to eight weeks.

Figure 5:
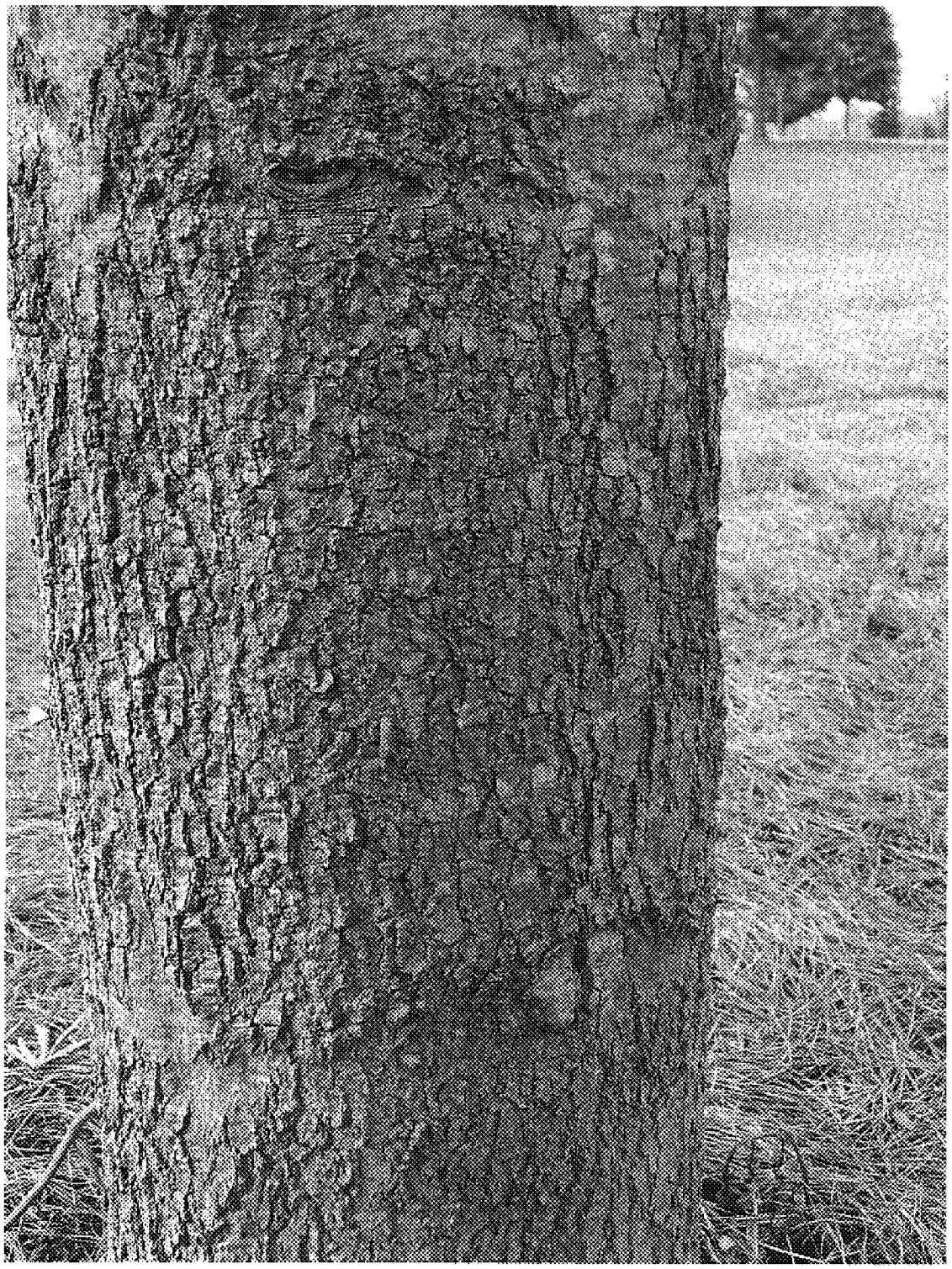
FIG. 5 is a close up of a typical section of the trunk of the original tree of the new variety.

Trunk: Bark is typical of the species, being smooth and gray (RHS 198B) on young trees, and gray (RHS 197B) and, with age, becoming roughened by irregular furrows and thick, more or less scaly ridges (see FIG. 5). Mature bark is grayed green (RHS 194A) in color, also typical of the species.

Figure 6:
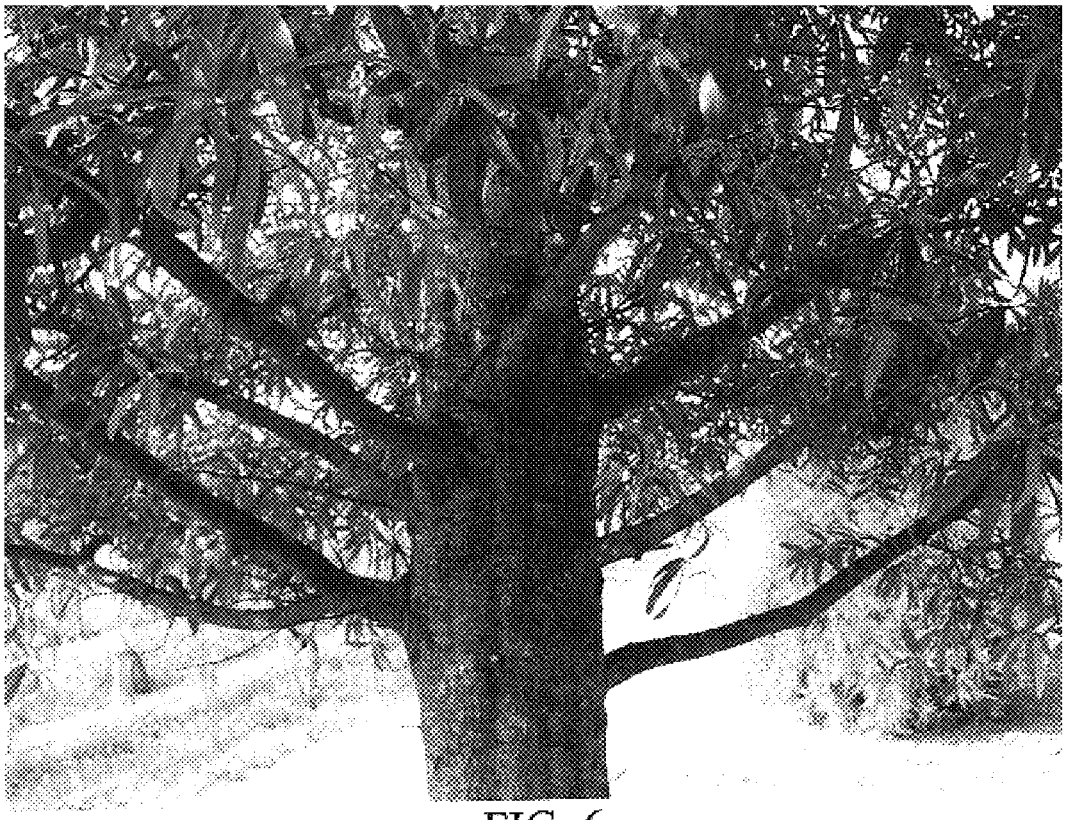
FIG. 6 is a close up of the branching habit of the new variety.

Branching habit: Denser than typical for the species (See FIGS. 1 and 2). Primary branches toward the top of the tree emerge at about a 45 degree angle to the leader and branch angle relative to the trunk tends to increase with age (see branches on lower portion of tree in FIG. 2 and FIG. 6).

Branches: One year old (new growth) branches are approximately ¼ inch in diameter with smooth texture and gray-green (RHS 143B) on the lower stem surface and orange-brown (RHS 175A) in color on the upper stem surface.

Figure 3:
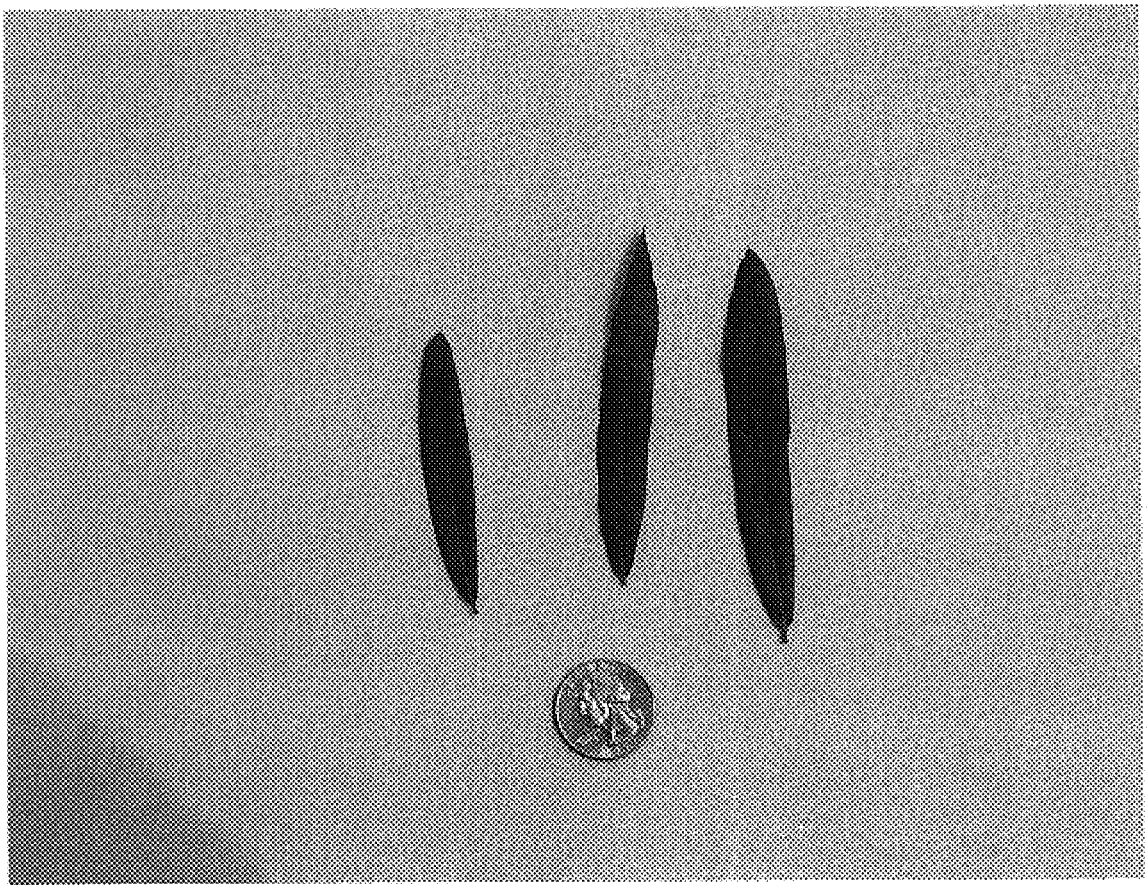
FIG. 3 is a close up of the top side of three single leaves from a tree of the new variety. The US Quarter Dollar in the picture provides a sizing reference.
Figure 4:
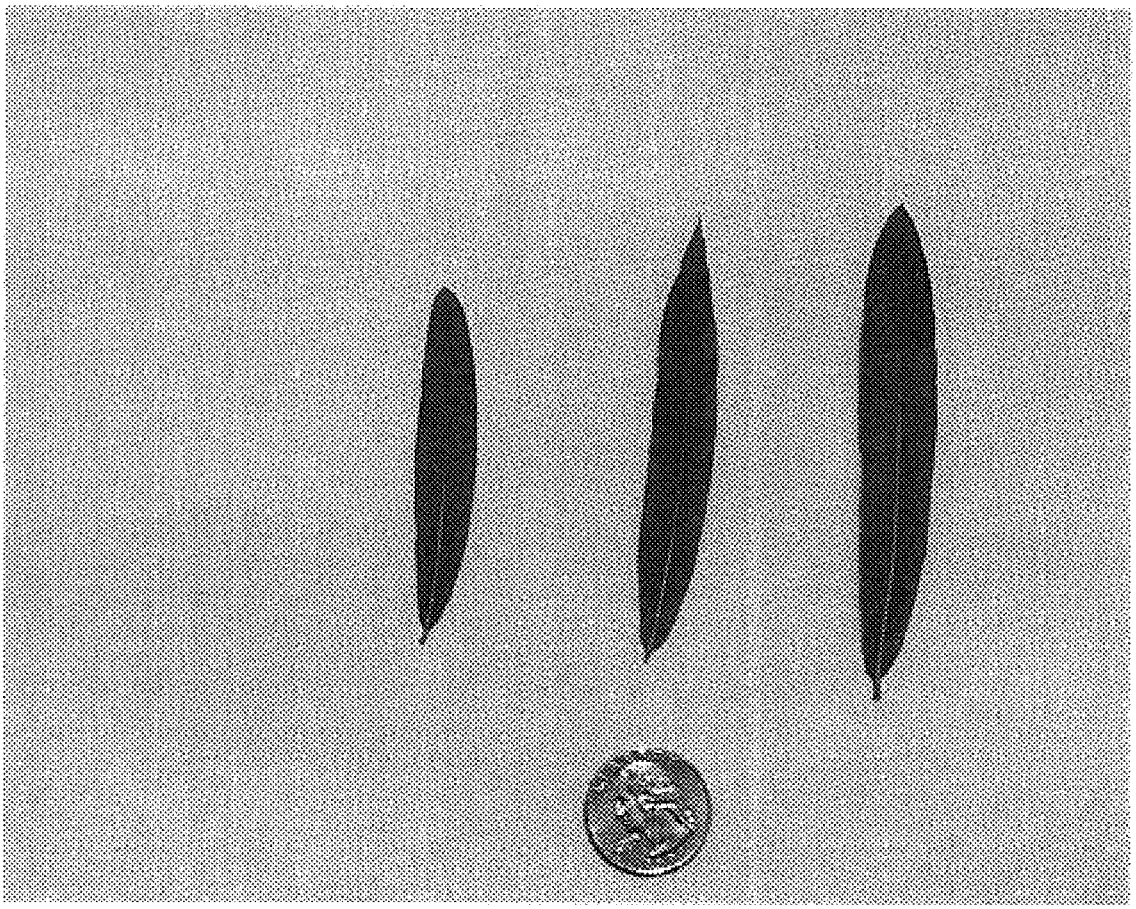
FIG. 4 is a close up of the underside of three single leaves of the new variety.

Foliage: Typical of the species. Leaves are alternate, simple; narrowly elliptical or lance-shaped, 2 to 5½ inches long, ⅓ to 1 inch wide; acute, slightly wavy and entire on margins, usually tipped with a bristle. Both the leaf apex and base are acute in shape. Leaves exhibit a pinnate venation pattern with light-green (RHS 145A) colored veins. Leaves emerge light green (RHS 143C) in spring, becoming darker green (RHS 139A) in summer. On mature leaves, the upper leaf surface (FIG. 3) is dark green (RHS 147A), and the lower leaf surface (FIG. 4) is a slightly lighter green (RHS 147B). Fall color is yellow. A typical petiole is approximately ¼ to ⅜ inch long, approximately 1/16 inch in thickness (diameter), and light green (RHS 144A) in color.

Buds: Typical of the species, being imbricate, ⅛ to ¼ inch long, ovoid, sharp-pointed, chestnut brown (RHS 165B) in color.

Flowers: Typical of the species. Willow Oaks, including the variety, are monoecious. Staminate catkins are pendent and clustered. Individual flowers are typically 4- to 7-lobed calyx enclosing about 6 or more stamens. Pistillate flowers are solitary or borne in spikes from axils of new leaves. Individual flowers usually consist of a 6-lobed calyx surrounding an ovary, the whole being partly enclosed in an involucre. Date of initial bloom (in Oconee County, Ga. is approximately April 1, with duration of approximately 10–14 days.

Fruit: Typical of the species. The acorn, to date observed only in the original tree, is solitary or paired, about ½ inch or less long and wide, subglobose, enclosed at the base by a thin saucer like cap. The acorn itself has alternating brown and blackish bands.

Root system: Typical of the species. Oaks typically have coarse root systems, but Willow Oak trees, including the new variety, have a more fibrous root system than other species within the genus.

Disease and pest resistance: Appears to be typical of the species; however, it has shown to have increased spider mite resistance.

Winter hardiness: Not yet determined, due to only being grown and observed in Oconee County, Ga. (USDA Zone 7).

I claim:

1. A new and distinct variety of Willow Oak tree named 'QPSTJ,' substantially as herein illustrated and described, characterized particularly as to novelty by its upswept branching habit, dense canopy, dominant central leader, unique red fall color, and relatively fast growth rate.

* * * * *